US012048565B2

(12) United States Patent
Calhoun et al.

(10) Patent No.: US 12,048,565 B2
(45) Date of Patent: Jul. 30, 2024

(54) SYSTEM AND METHODS FOR DIFFERENTIATING MENTAL DISORDERS AND PREDICTING MEDICATION-CLASS RESPONSE IN PATIENTS USING RESTING STATE FUNCTIONAL MRI SCANS

(71) Applicant: UNM Rainforest Innovations, Albuquerque, NM (US)

(72) Inventors: Vince Calhoun, Albuquerque, NM (US); Jing Sui, Albuquerque, NM (US)

(73) Assignee: UNM RAINFOREST INNOVATIONS, Albuquerque, NM (US)

( * ) Notice: Subject to any disclaimer, the term of this patent is extended or adjusted under 35 U.S.C. 154(b) by 998 days.

(21) Appl. No.: 16/961,626

(22) PCT Filed: Jan. 15, 2019

(86) PCT No.: PCT/US2019/013617
§ 371 (c)(1),
(2) Date: Jul. 10, 2020

(87) PCT Pub. No.: WO2019/140435
PCT Pub. Date: Jul. 18, 2019

(65) Prior Publication Data
US 2020/0337650 A1 Oct. 29, 2020

Related U.S. Application Data

(60) Provisional application No. 62/626,224, filed on Feb. 5, 2018, provisional application No. 62/617,561, filed on Jan. 15, 2018.

(51) Int. Cl.
*G16H 50/30* (2018.01)
*A61B 5/00* (2006.01)
(Continued)

(52) U.S. Cl.
CPC .......... *A61B 5/7275* (2013.01); *A61B 5/0042* (2013.01); *A61B 5/055* (2013.01);
(Continued)

(58) Field of Classification Search
CPC ..... A61B 5/7275; A61B 5/0042; A61B 5/055; A61B 5/165; A61B 5/7267; G16H 50/30; G16H 50/70; G16H 50/20; G06N 20/10
See application file for complete search history.

(56) References Cited

U.S. PATENT DOCUMENTS 8,886,283 B1 * 11/2014 Chen ................... A61B 5/4064
382/128
2005/0267357 A1 12/2005 Rao
(Continued)

FOREIGN PATENT DOCUMENTS

CN 107507162 A * 12/2017
WO 2009157945 12/2009

OTHER PUBLICATIONS

International Search Report and the Written Opinion of the ISA/RU, Feb. 27, 2019.

*Primary Examiner* — Shefali D Goradia
*Assistant Examiner* — D J Dhooge
(74) *Attorney, Agent, or Firm* — Valauskas Corder LLC

(57) ABSTRACT

The present invention is directed to a system and methods of predicting undiagnosed mental disorders in a patient and determining the best medication-class treatment for the mental disorder through the analysis of functional magnetic resonance imaging of functional connectivity of the brain representative of a certain mental disorder.

19 Claims, 12 Drawing Sheets

(51) Int. Cl.
  *A61B 5/055* (2006.01)
  *A61B 5/16* (2006.01)
  *G06N 20/10* (2019.01)
  *G16H 20/70* (2018.01)
  *G16H 50/20* (2018.01)
  *G16H 50/70* (2018.01)

(52) U.S. Cl.
  CPC ............ *A61B 5/165* (2013.01); *A61B 5/7267* (2013.01); *G06N 20/10* (2019.01); *G16H 20/70* (2018.01); *G16H 50/20* (2018.01); *G16H 50/30* (2018.01); *G16H 50/70* (2018.01)

(56) References Cited

U.S. PATENT DOCUMENTS

| | | | |
|---|---|---|---|
| 2006/0084858 A1* | 4/2006 | Marks | A61B 5/16 600/407 |
| 2010/0249573 A1* | 9/2010 | Marks | G06F 18/00 600/411 |
| 2011/0028827 A1 | 2/2011 | Sitaram | |
| 2016/0228056 A1* | 8/2016 | Hooker | A61B 6/508 |
| 2017/0251985 A1 | 9/2017 | Howard | |

* cited by examiner

Table 1: Demographic and Clinical Data of Participant Scans

| Group | BD | MDD | HC |
|---|---|---|---|
| Number* | 35 | 35 | 33 |
| Age (years, mean±SD) Range | 21.4±2.8 16-27 | 19.6±2.6 16-25 | 20.2±2.0 17-24 |
| Sex (M/F) | 17/18 | 10/25 | 13/20 |

*Participants with repeat scans are treated as distinct individuals because of different ages at each scan. This included three BD participants, separated by 1, 2 and 3 years plus 1 repeat scan of an MDD participant scanned 2 years later.

FIG. 5

Table 2: DIGS Diagnosis, Clinical Diagnosis & Medication-Class and Vote of Classifier

| ID | Age | Sex | DIGS Dx | Chart Dx on Entry | Rx at Scan | Rx of Response[1] | BD | MDD | Voting Results |
|---|---|---|---|---|---|---|---|---|---|
| 1308 | 22 | M | BD-I | MDD | AD | AP | 33.7% | 46.3% | BD |
| 1310 | 20 | M | BD-I | MDD | AD | AD | 16.6% | 83.4% | MDD |
| 1322 | 24 | M | MDD | MDD | None | MS,AP | 75.8% | 24.2% | BD |
| 1325 | 18 | F | none | n.a. | None | n.a. | 9.6% | 90.4% | MDD |
| 1348[a] | 21 | M | BD-I | BD-I | MS | MS,AP | 33.8% | 66.2% | MDD |
| 1364 | 19 | F | MDD | MDD vs BD | MS | MS | 76.4% | 23.6% | BD |
| 1368 | 19 | M | MDD | MDD vs BD | MS | MS | 77.0% | 23.0% | BD |
| 1372 | 19 | M | BD-II | None[b] | None | none | 21.3% | 78.7% | MDD |
| 1378 | 28 | M | MDD | MDD vs BD | AD | none | 41.9% | 58.1% | MDD |
| 1392 | 19 | F | BD-II | MDD vs BD | MS,AD | MS | 52.2% | 47.8% | BD |
| 1395 | 19 | F | MDD | MDD vs BD | None | none | 36.7% | 63.3% | MDD |
| 1407 | 19 | M | BD-II | MDD vs BD | AD | AD | 11.3% | 88.7% | MDD |

[1] The class of medication that was effective at the time the patient was stable, at the last time of evaluation as determined clinically and by chart review, to include only ADs, MSs or APs.

[a] This patient was ultimately diagnosed with schizoaffective disorder due to persistent paranoid ideation.

[b] This patient was diagnosed with ADHD and GAD, but no mood disorder

Rx = medication, DIGS = Diagnostic Interview for Genetic Studies, Dx = diagnosis, AD = antidepressant, MS = mood stabilizer, AP = antipsychotic

FIG. 6

TALARIACH TABLE OF THE SPATIAL MAPS OF THE SELECTED 5 IC'S

| BRAIN AREA | BRODMANN AREA | VOLUME (CC) | MAX Z VALUE (X,Y,Z) |
|---|---|---|---|
| IC2 | | | |
| SUPERIOR TEMPORAL GYRUS | 22,38 | 2.9/5.1 | 12.4(-39,8,-13)/16.6(42,8,-13) |
| INFERIOR FRONTAL GYRUS | 13,47 | 0.9/1.8 | 9.5(-39,14,-13)/14.2(42,14,-13) |
| INSULA | 13 | 2.0/2.0 | 10.0(-42,-3,-5)/11.4(45,6,-5) |
| | | | |
| IC16 | | | |
| INFERIOR FRONTAL GYRUS | 9,47 | 1.3/3.1 | 7.0(-53,17,-6)/9.4(50,17,-6) |
| SUPERIOR TEMPORAL GYRUS | 22,38 | 1.3/1.7 | 7.6(-50,14,-6)/9.2(48,17,-8) |
| SUPERIOR FRONTAL GYRUS | 6,8 | 2.5/2.8 | 7.0(0,14,49)/7.0(3,18,60) |
| MEDIAL FRONTAL GYRUS | 6,8,32 | 1.0/1.2 | 6.4(0,11,46)/6.0(3,14,46) |
| CINGULATE GYRUS | 32 | 1.0/1.3 | 5.8(0,22,32)/5.7(3,16,38) |
| MIDDLE FRONTAL GYRUS | 6,9,46 | 0.2/1.2 | 3.8(-48,5,44)/4.5(53,16,27) |
| | | | |
| IC6 | | | |
| PRECUNEUS | 7,31 | 7.0/7.5 | 11.2(-3,-71,39)/11.7(3,-68,42) |
| CUNEUS | 7 | 0.3/0.2 | 7.8(0,-65,31)/6.3(3,-68,31) |
| CINGULATE GYRUS | 23,31 | 1.1/0.6 | 6.3(0,-25,26)/5.4(3,-22,26) |
| SUPERIOR PARIETAL LOBULE | 7 | 1.1/0.4 | 5.0(-3,-64,56)/5.4(9,-67,53) |
| POSTERIOR CINGULATE | 23,29 | 0.2/0.3 | 4.4(-3,-37,24)/5.0(3,-37,24) |
| INFERIOR PARIETAL LOBULE | 7,39,40 | 1.7/0.4 | 4.9(-42,-53,52)/3.8(45,-56,50) |

FIG. 7

| IC1 | | | |
|---|---|---|---|
| CAUDATE | | 1.1/1.1 | 14.0(-6,1,11)/13.5(6,3,8) |
| THALAMUS | | 0.8/1.2 | 12.4(-6,-2,8)/10.6(6,-2,8) |
| PARAHIPPOCAMPAL GYRUS | 27,30 | 0.3/0.2 | 5.3(-12,-35,-3)/7.3(9,-38,-1) |
| | | | |
| IC11 | | | |
| INFERIOR PARIETAL LOBULE | 40 | 5.0/2.6 | 10.1(-45,-35,57)/9.1(48,-32,57) |
| POSTCENTRAL GYRUS | 1,2,3,5,7,40 | 5.0/5.1 | 9.1(-50,-29,54)8.6(42,-35,60) |
| SUPERIOR PARIETAL LOBULE | 7 | 2.3/1.7 | 6.7(-36,-47,60)/6.0(36,-47,60) |
| PRECENTRAL GYRUS | 4,6 | 0.1/0.6 | 4.9(-59,-18,40)/5.2(59,-18,42) |
| MIDDLE TEMPORAL GYRUS | 37 | 0.2/0.0 | 3.8(-53,-61,-2)/NA |
| INFERIOR FRONTAL GYRUS | 9,46 | 0.2/0.2 | 3.6(-53,10,30)/3.6(48,41,6) |
| MIDDLE FRONTAL GYRUS | 46 | 0.0/0.1 | NA/3.5(48,44,9) |

FIG. 7 Cont.

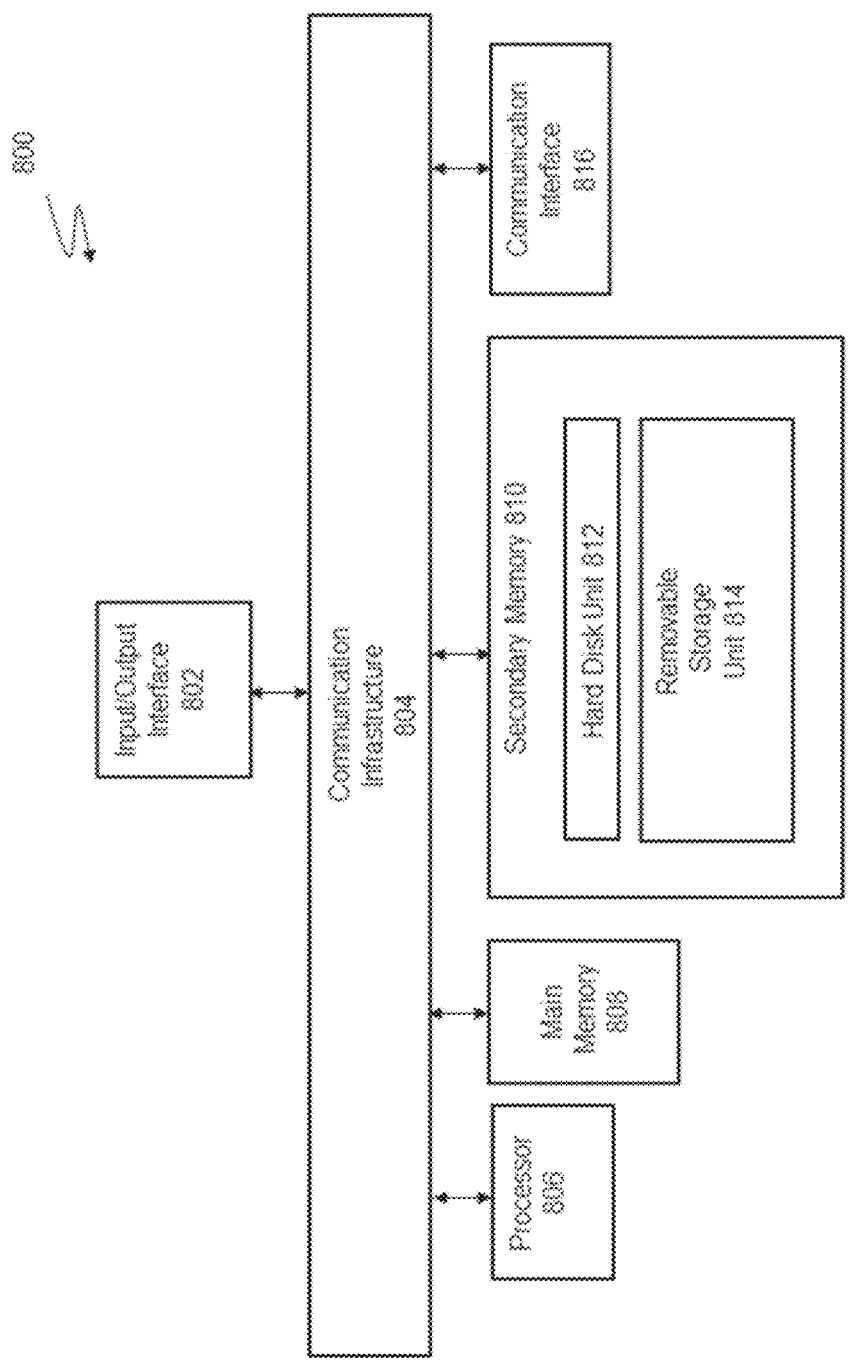

SYSTEM AND METHODS FOR DIFFERENTIATING MENTAL DISORDERS AND PREDICTING MEDICATION-CLASS RESPONSE IN PATIENTS USING RESTING STATE FUNCTIONAL MRI SCANS

CROSS-REFERENCE TO RELATED APPLICATIONS

This invention claims priority to U.S. Provisional Patent Application Ser. No. 62/617,561 filed Jan. 15, 2018, and U.S. Provisional Patent Application Ser. No. 62/626,224 filed Feb. 5, 2018, both of which are incorporated herein by reference in their entireties.

STATEMENT REGARDING FEDERALLY SPONSORED RESEARCH

This invention was made with government support under Grant No's. P20GM103472, 1R01EB006841, and R01EB005846 awarded by the National Institutes of Health. The government has certain rights in the invention.

FIELD OF THE INVENTION

The invention generally relates to the diagnosis of mental disorders. More particularly, the invention relates to a system and methods for predicting mental disorders in subjects having an unknown mental disorder diagnosis through the analysis of functional magnetic resonance imaging of functional connectivity of the brain representative of a certain mental disorder and predicting a medication-class treatment response to the mental disorder.

BACKGROUND OF THE INVENTION

Mental disorders often times may be painful, debilitating, and very costly for the affected individual, their family, and society as a whole. The World Health Organization estimates that over 1 billion people worldwide suffer from some form of mental disorder. Further, it is estimated that—by the year 2030—over 6 trillion dollars may be spent on treating the mental disorders. A further 16 billion dollars may be lost through an estimated 12 billion days of work lost each year due to the burden of mental disorder.

In the Unites States of America, approximately one in five adults experiences a mental disorder in a given year, 18.1% of adults experience an anxiety disorder, such as posttraumatic stress disorder, obsessive-compulsive disorder and specific phobias, 6.9% of adults have at least one major depressive episode each year, and 1.1% of adults live with schizophrenia.

The consequences of lack of treatment are significant. In the United States of America, mental disorders are the third most common cause of hospitalization for both youth and adults aged 18-44. Suicide is the tenth leading cause of death, and the second leading cause of death for those aged 15-24. And each day, approximately 18-22 Armed Forces veterans die by suicide.

A key factor in treatment of mental disorders is proper diagnosis. Typically, the standard method of diagnosing mental disorders includes either the use of the *Diagnostic and Statistical Manual of Mental Disorders*, Fifth Edition, American Psychiatric Association, (2013), Arlington, VA ("DSM") or the *International Statistical Classification of Diseases and Related Health Problems (ICD), Chapter 5: Mental and behavioral disorders,* 10th Revision (ICD-10), 1994, Geneva: World Health Organization ("ICD"). Both of these standards primarily involve diagnosis using conversation with the patient regarding symptoms and behavior. This has the disadvantage of being subjective—that is, based on the interviewer's own perceptions—that may lower the diagnostic reliability and the resultant treatment and, sometimes, may result in two clinicians forming two different diagnoses of the same patient.

These difficulties may be exemplified, for example, in efforts to differentiate bipolar disorder ("BD") from major depressive disorder ("MDD") using the DSM which may be challenging in patients without obvious mania. Since patients with BD generally spend more time in depressive than manic states, BD is often misdiagnosed as MDD. BD patients go 6-10 years without a proper diagnosis. And while the adoption of a spectrum approach to mood disorder diagnosis may be appealing, the treatment response of patients to various medication classes, (e.g., antidepressants versus mood stabilizers) suggests the existence of a fundamental difference between MDD and BD. Further, mood stabilizers often do not effectively treat MDD while antidepressants may make BD worse. Inadequately treated BD may be costly to the medical system and may exacerbate human suffering. Thus, obtaining the correct mood diagnosis and the correct medication-class is imperative to best support recovery of the patient One promising tool available to healthcare workers that may facilitate the diagnosis of mental disorders is magnetic resonance imaging ("MRI"). MRI produces a sequence, or "time series," of high-resolution three-dimensional images of human anatomy and is widely used to diagnose or stage disease without exposing a subject to ionizing radiation.

A variation of MRI—functional magnetic resonance imaging ("fMRI")—is a method for identifying a change in a level of activation of a region of the brain of a subject. A level of activation of a region of the brain may change when the subject receives a stimulus, performs a task, or experiences another experimental condition. Like an MRI image, each fMRI image represents a three-dimensional "snapshot" of the brain volume of the subject but adds the additional dimension of a unique time point at which the image was recorded. Each 3D representation of the brain volume of the subject may show a level of neuronal activation at the recording time of the image at each three-dimensional point comprising the brain volume. A difference between two activation levels may be represented in the image as a corresponding difference in color, brightness, density, or another characteristic of a voxel of the image. In some implementations, a level of activation of a region of a brain volume may be a function of a blood oxygenation level dependent ("BOLD") signal that identifies a level of neuronal activation in that region.

An fMRI series of images may be analyzed to identify interactions between regions of a brain that may work together to perform a particular function or to respond to a specific class of stimulus, a relationship known as "functional connectivity." Such relationships, in some cases, may be inferred from correlations or covariances among time measurements associated with the changes in levels of activation of such regions. For example, two regions of the brain may be deemed functionally connected if, each time a subject experience a stimulus, such as a pinprick, those two areas of the brain are activated simultaneously.

Numerous efforts have successfully distinguished DSM-diagnosed BD from MDD using fMRI. However, these studies involved patients with diagnoses made according to the DSM or related criteria, with patients not meeting such criteria excluded from study. These imaging methods were created to classify those patients according to this DSM "gold standard". The lack of complexity in the patients included in these studies leads to questions about the utility of such methods as a facilitative strategy in real clinical work.

This same concern about complexity in the "real world" of clinical care also applies to randomized clinical trials evaluating medication (and other) treatment responses within specific patient populations. The careful selection of research participants with clear-cut DSM diagnoses leads to challenges in implementing treatment recommendations in the clinical reality of multiple co-morbid diagnoses, fluctuating time-courses of illness, uncertain reporting of personal and family histories, and unclear responses to past medication trials.

In clinical work, diagnoses often may not be as well-defined as in research protocols. The situations most demanding of a biologically-based classification methods are, in fact, those in which the DSM classification may be unclear, and the clinical impression may be confusing. Yet practicing clinicians still must prescribe a treatment regimen for such complicated patients. Additionally, in emerging adults without a long personal history of psychiatric illness, clinical presentation is often not classical. Emerging adults with mood disorders often face a long future of treatment responsiveness or refractoriness, making it imperative to choose the right medication-class to optimize recovery.

Accordingly, there is a need for a new system and methods of easily and accurately predicting a mental disorder and providing to the user a proper medication-class for use as a treatment. The present invention satisfies this need.

SUMMARY OF THE INVENTION

The invention is directed to a system and methods of differentiating mental disorders and predicting medication-class response in patients with an unclear mental disorder diagnoses using a predictive classifier. Generally, certain embodiments of the invention may use a database of functional magnetic resonance imaging (fMRI) resting state data from healthy subjects and patients with a known mental disorder diagnosis and a respective medication-class used to attain sustained recovery. A user of the invention may choose an appropriate database according to the type of mental disorder or mental illness that a user wishes to differentiate in a patient. For example, if the patient is dealing with depressive symptoms or signs of bipolar disorder, then a database consisting of fMRI data of major depressive disorder and bipolar disorder may be used to train the classifier in order to best identify the mental disorder of the undiagnosed patient and an appropriate medication-class that may be used to treat the disorder. Ultimately, the performance of the predictive classifier may be optimized by using the database that most closely resembles the symptoms of the unknown patient.

The fMRI data from the appropriate database(s) may be pre-processed and used to create prior maps of functional connectivity networks. These prior maps may be created using a predictive classifier that is trained and cross-validated on the appropriate database using maximally spatially independent components (ICs), constructing a similarity matrix among subjects, partitioning the matrix in kernel space, and optimizing the classifier and IC combinations. The ICs may be extracted using spatially constrained independent component analysis (ICA) that may include, for example, ICA on two-stage principle component analysis reduced data. The ICs may correspond to the functional connectivity networks of the brain. A component selection technique may be used to identify the optimal IC combinations.

An ensemble classifier then may be constructed from a base classifier that itself may be constructed from one or more of the prior maps. The classifiers in the ensemble classifier may use different IC combinations (i.e., brain networks) or classification methods. Preferably, embodiments of the invention may use an ensemble Support Vector Machine classifier, but any classifier may be used (e.g., Perceptron, Naïve Bayes, Decision Tree, Logistic Regression, K-Nearest Neighbor, and Artificial Neural Networks).

The fMRI resting state pre-processed data from patients with an unknown diagnosis also may be processed through a spatially constrained ICA based upon the prior maps created from the appropriate database. The classifier or ensemble classifier trained on data from the database then may be used to predict the most likely mental disorder and a medication class response for these patients.

Certain embodiments of the invention may be used to view a mental disorder on a spectrum instead of in individual categories. This may be accomplished through the use of a regression method in place of a classifier. Additionally, a feature selection method such as forward or backward elimination may be used to select the best ICs for prediction of the mental disorder and the medication-class response.

One certain preferred embodiment of a system and methods of the invention comprises collecting fMRI scans—that include one or more images of the brain—of healthy subjects, patients with a known mental disorder diagnosis and a medication-class response to the mental disorder, and unknown patients having an undiagnosed mental disorder. The fMRI scans from the healthy subjects and patients with known mental disorders and medication-class treatment response may be stored in a database according to the diagnosed mental disorder and may be used as training data. The training data may be pre-processed and used to create one or more prior maps of optimal functional connectivity networks of the brain. A classifier then may be generated from the training data from the selected database and applied to the fMRI scans of unknown patients in order to predict a mental disorder and a medication-class response of the unknown patients.

In certain preferred embodiments of the invention, the pre-processing step of the fMRI scans may include, for example, the processes of slice time correction, realignment, spatial normalization, and smoothing. In other embodiments of the invention, pre-processing may include correcting each image of a scan for an acquisition time delay amount, realigning each of the images to a first volume, and spatially normalizing each image to Montreal Neurological Institute (MNI) space by diffeomorphic anatomical registration using exponentiated Lie algebra (DARTEL). The images also may be spatially smoothed at the half maximum (FWHM) Gaussian kernel.

According to certain preferred embodiments of the invention, prior maps of brain connectivity also may be created by estimating the maximally spatially independent components from the fMRI scans using spatially constrained independent component analysis. And a similarity matrix may be created between the healthy subjects and the patients with a known mental disorder and medication-class response based on the spatially constrained independent component analysis. The similarity matrix then may be partitioned into a kernel space. A step-wise forward component also may be selected using a validation of classifiers and independent component combinations. A final classifier then may be created using optimal independent component combinations from the prior maps of the training data in a spatial or a temporal domain.

The prediction of a mental disorder and identification of an associated medication-class response of an unknown patient with an unknown mental disorder may be achieved through the application of the classifier—created from the training data—to fMRI image data captured from the unknown patients. The fMRI data may be subjected to a spatially constrained independent component analysis using the prior maps of the training data.

Advantageously, embodiments of the invention may be used to differentiate among two or more mental disorders (including no mental disorder) in unknown patients. The classifier also may differentiate among the groups in the database used to train the classifier.

Advantageously, embodiments of the invention may be used in instances of difficult-to-diagnose patients. The invention reframes the question that biologically based classification methods and imaging biomarkers most urgently need to answer: what medication class is most likely to help an individual patient attain sustained recovery?

These and other exemplary features and advantages of the present invention will become clear from the following description with reference to the accompanying drawings.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the presented detailed description. The description and accompanying drawings may highlight a certain specific example, or a certain aspect of the invention. However, one skilled in the art will understand that portions of the example or aspect may be used in combination with other examples or aspects of the invention.

FIG. 5 illustrates the demographic and clinical data of participants in a study to differentiate BD and MDD;

FIG. 6 illustrates DIGS diagnosis, Clinical diagnosis, Medication-class, and the prediction of a mental disorder using an embodiment of a classifier of the invention;

FIG. 7 illustrates a Talariach table of the spatial maps of selected Independent Components; and FIG. 8 illustrates an exemplary computer system that may be used with the invention.

DETAILED DESCRIPTION OF THE INVENTION

Embodiments of the present invention are directed towards a system and methods of differentiating mental disorders and predicting the appropriate medication-class for treatment of the mental disorder through the use of a predictive classifier. Advantageously, this classifier may be used during the early stages of treatment of mentally ill patients having an unclear diagnosis to recommend to medical personnel using the classifier a medication class that may be used to help the patient achieve a sustained recovery to euthymia. As used in this Application, a "mental illness" or "mental disorder" or "mental disease" or "psychiatric or neuropsychiatric disease or illness or disorder" refers to mood disorders, psychotic disorders (e.g., schizophrenia, schizoaffective disorder, schizophreniform disorder, delusional disorder, brief psychotic disorder, and shared psychotic disorder), personality disorders, anxiety disorders (e.g., obsessive-compulsive disorder) as well as other mental disorders such as substance-related disorders, childhood disorders, dementia, autistic disorder, adjustment disorder, delirium, multi-infarct dementia, and Tourette's disorder as described in the DSM. Typically, such disorders have a genetic and/or a biochemical component as well.

A "mood disorder" refers to disruption of feeling tone or emotional state experienced by an individual for an extensive period of time. Mood disorders include major depression disorder (i.e., unipolar disorder), mania, dysphoria, bipolar disorder, dysthymia, cyclothymia and many others. See, e.g., the DSM.

"Major depression disorder," "major depressive disorder," or "unipolar disorder" refers to a mood disorder involving any of the following symptoms: persistent sad, anxious, or "empty" mood; feelings of hopelessness or pessimism; feelings of guilt, worthlessness, or helplessness; loss of interest or pleasure in hobbies and activities that were once enjoyed, including sex; decreased energy, fatigue, being "slowed down"; difficulty concentrating, remembering, or making decisions; insomnia, early-morning awakening, or oversleeping; appetite and/or weight loss or overeating and weight gain; thoughts of death or suicide or suicide attempts; restlessness or irritability; or persistent physical symptoms that do not respond to treatment, such as headaches, digestive disorders, and chronic pain. Various subtypes of depression are described in, e.g., the DSM.

"Bipolar disorder" is a mood disorder characterized by alternating periods of extreme moods. A person with bipolar disorder experiences cycling of moods that usually swing from being overly elated or irritable (mania) to sad and hopeless (depression) and then back again, with periods of normal mood in between. Diagnosis of bipolar disorder is described in the DSM. Bipolar disorders include bipolar disorder I (mania with or without major depression) and bipolar disorder II (hypomania with major depression).

Figure 1:
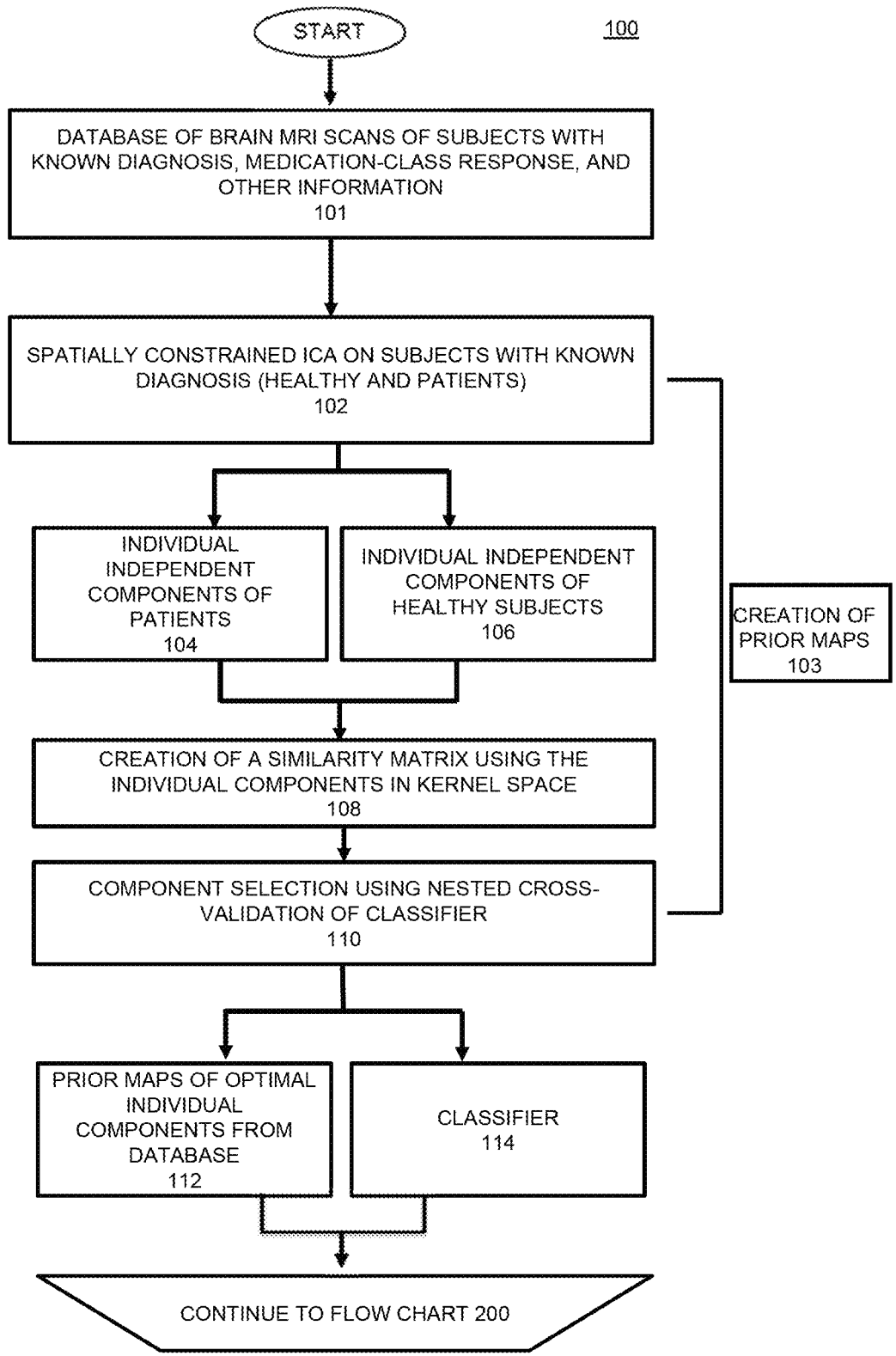
FIG. 1 illustrates a flow chart of one embodiment of a method of the invention for creation of prior maps and a classifier from healthy subjects and patients with known diagnosis.

FIG. 1 generally illustrates a flow chart 100 of the steps performed by one embodiment of the invention to create prior maps of brain functional connectivity and a predicative classifier. As shown at step 101, MRI scans, and more preferably, fMRI scans that may include a plurality of images of brain slices may be captured from one or more individuals using an appropriate fMRI device or devices. The individual that are used in the capture of the fMRI scans may include one or more healthy subjects and one or more patients having a known mental disorder diagnosis and a known treatment response to a medication-class used to treat the disorder. This fMRI data may be organized into various databases according to the type of mental disorder. For example, a database directed to BD may contain only fMRI data from subjects diagnosed with BD and treated using a certain medication-class.

Preferably, the plurality of images from the fMRI scans from each database from flow chart 100 may be pre-processed. Pre-processing of fMRI resting state data using statistical parametric mapping software may include the techniques of slice time correction, realignment, spatial normalization of functional image to structural image, smoothing, removing the linear drift, band-pass filtering, spatial normalization to 3 mm MNI space based on structure images, and regressing out the nuisance covariants such as described in Smith et al., *Advances in Functional and Structural MR image Analysis and Implementation as FSL*, NeuroImage 23 (2004), pp. 208-219.

The pre-processed data of step 101 may be used to create prior maps 103 of brain functional connectivity as detailed in steps 102 through 110. Creation of prior maps of optimal functional connectivity networks may include the use of one or more databases of fMRI resting state data of healthy subjects and patients with known psychiatric diagnosis confirmed by medication-class use in treatment to attain sustained recovery. The appropriate database may be chosen depending upon the type of mental disorder that the user wants to differentiate in an unknown patient. For example, if the unknown patients are dealing with depression symptoms, then a database comprising of fMRI data of major depressive disorder and/or bipolar disorder may be selected from which the fMRI data may be drawn.

In step 102, the pre-processed data from the selected database may be subjected to a spatially constrained independent component analysis (ICA) to extract spatially independent component (IC) maps from the patients with known mental disorder diagnosis 104 and the healthy subjects 106, as well as group level IC maps. ICA is a statistical technique that separates a set of signals, in this case fMRI data, into independent—uncorrelated and non-Gaussian—spatiotemporal components. Certain embodiments of the invention may use group information guided ICA (GIG-ICA) as described, for example, in Du et al., *Group information guided ICA for fMRI data analysis*. NeuroImage, Volume 69, 1 Apr. 2013, Pages 157-197). Advantageously, GIG-ICA estimated individual IC maps may be more accurate the IC maps created only using ICA. GIG-ICA also may estimate accurately corresponding matched components from new data sets (e.g. the unknown subjects (UNK) with an unknown mental disorder diagnosis) for classification purposes. Embodiments of the method automatically may select the relevant networks and ICs. Exemplary IC's may include one or more of, but are not limited to, the Inferior Parietal Lobule, Postcentral Gyrus, Superior Parietal Lobule, Precentral Gyrus, Inferior Frontal Gyrus, Middle Frontal Gyrus, Middle Temporal Gyrus, Inferior Temporal Gyrus, Precuneus, Cuneus, Cingulate Gyrus, Inferior Parietal Lobule, Superior Parietal Lobule, Posterior Cingulate, Superior Temporal Gyrus, Inferior Frontal Gyrus, Superior Frontal Gyrus, Medial Frontal Gyrus, Middle Frontal Gyrus, Cingulate Gyrus, Caudate, Thalamus, Parahippocampal Gyrus, Superior Temporal Gyrus, Inferior Frontal Gyrus, and Insula.

As shown in step 108, a similarity matrix among the subjects in kernel space may be computed. Various distance metrics may be used to construct the similarity matrix such as Riemannian similarity/distance measure (Bjöerck et al., *Numerical Methods for Computing Angles Between Linear Subspaces*. Technical Report. Stanford University, CA, USA (1971)) computed based on principal angles between spatial component maps of different individuals that may represent subspace similarities between individuals spanning a subset of ICs.

According to step 110, a component selection method and machine learning classifier may be used to find the optimal IC combinations on the basis of how well the classifier performs on patients with known diagnosis from the database. Various types of component selection techniques may be used for different type of databases. Examples include but are not limited to forward component selection and backward component selection.

The optimal group-discriminative IC combinations may be selected using nested cross-validation of the classifiers. Various types of validation techniques may be used to test the effectiveness of the classifier. The validation technique may change with the type of dataset under consideration. Examples include but are not limited to 10-fold nested cross validation or splitting the dataset in half between training and validation sets. Finally, a classifier may be constructed using optimal IC combinations from the training data 114. These optimal IC combinations may be used as prior maps 112.

Various types of classifiers may be used to determine the optimal ICs in the spatial or temporal domains and to predict the medication-class response and mental disorders. Suitable classifiers include, but are not limited to, Support Vector Machines, Perceptron, Naïve Bayes, Decision Tree, Logistic Regression, K-Nearest Neighbor, Artificial Neural Networks, random forest, and deep learning. One or more of these classifiers, each using a different brain networks (i.e., group of ICs) may be used together in an aggregated classifier to make the final prediction of both the mental disorder and medication-class response. Based on the type of training datasets available, a user may choose a classifier that works best with a particular dataset. A regression method may be used instead of a classifier in order to view a mental disorder on a spectrum instead of in categories.

Figure 2:
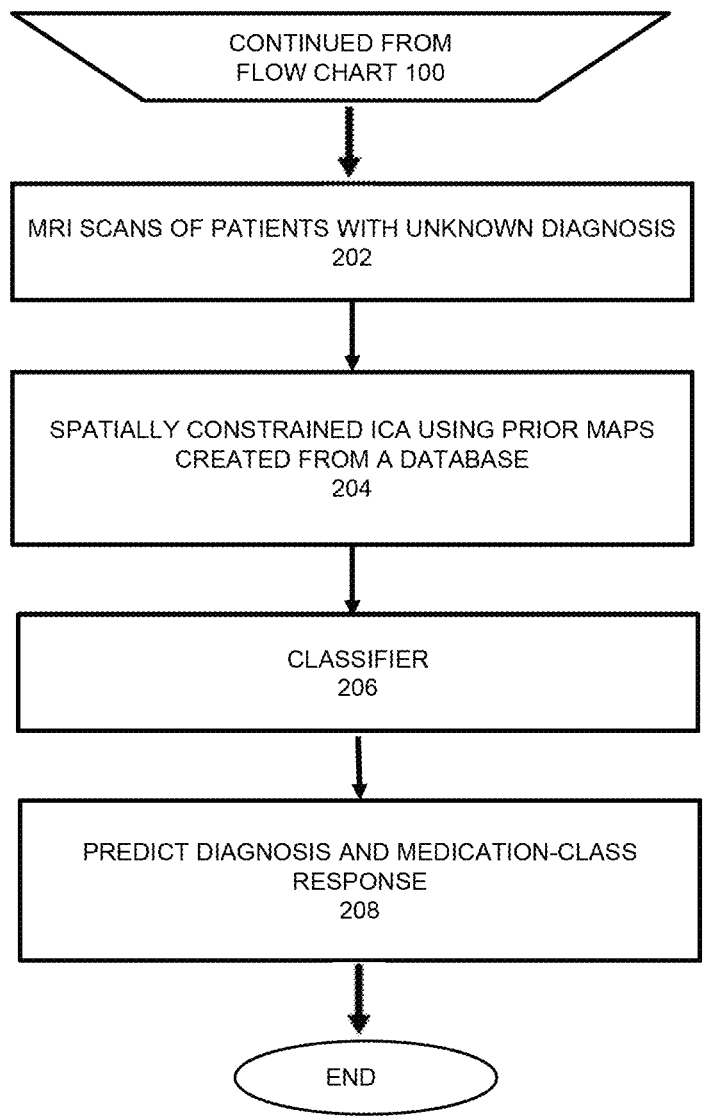
FIG. 2 illustrates a flow chart of one embodiment of a method of the invention for prediction of a mental disorder and a medication-class response in patients with an unknown mental disorder diagnosis.

With reference to the flow chart 200 shown in FIG. 2, step 202 shows the fMRI resting state data from patients with unknown diagnosis may be subjected to spatially constrained ICA using the prior maps created from the one or more databases 204. In steps 206, 208, the previously generated classifier may then be used to select the labels of each unknown patient's fMRI resting state data for individual subject classification to provide an output that may include a prediction, such a percentage of likelihood, of the type of mental disorder and the medication-class that may help the patient attain sustained recovery. Group membership for each new subject may be predicted by calculating the spatial components via spatially constrained ICA and entering each spatial component independently into a subspace representation. Importantly, the unknown patient information is not used in either the training or testing stages, ensuring an unbiased prediction. Thus, each patient classification represents an individual test of the classification method at the single subject level.

Medication-classes used in treating various disorders may include, but are not limited to, antidepressants, antianxiety, antipsychotics, mood stabilizers, and stimulants. And one or more medications within each class may be used to treat a mental disorder. Furthermore, treatment of a mood disorder also may include the use of medications from one or more medication classes.

Antidepressant medication may be used to treat depression, anxiety and sometimes other conditions. These medications may improve symptoms such as sadness, hopelessness, lack of energy, difficulty concentrating and lack of interest in activities. Antidepressants may include selective serotonin reuptake inhibitors, serotonin and norepinephrine reuptake inhibitors, atypical antidepressants, tricyclic antidepressants, and monoamine oxidase inhibitors. Exemplary antidepressant medications may include, but are not limited to, Atomoxetine (Strattera) Amitriptyline (Elavil®), Bupropion (Aplenzin®, Wellbutrin®), Imipramine (Tofranil®), Citalopram (Celexa®), Clomipramine (Anafranil®), Duloxetine (Cymbalta®), Desvenlafaxine (Pristiq®), Desyrel (Trazodone®), Doxepin (Sinequan®), Escitalopram (Lexapro®), Eszopiclone (Lunesta®), Fluoxetine (Prozac®), Fluoxetine and olanzapine (Symbyax®), Fluvoxamine (Luvox®), Isocarboxazid (Marplan®), Khedezla (Dexvenlafaxine ER®), Levomilnacipran (Fetzima®), Mirtazapine (Remeron®), Nefazodone (Serzone®), Nortriptyline (Pamelor®), Paroxetine (Paxil®), Phenelzine (Nardil®), Selegiline transdermal system (Emsam®), Sertraline (Zoloft®), Trazodone (Desyrel®), Tranylcypromine (Parnate®), Vilazodone (Viibryd®), and Venlafaxine (Effexor®).

Antianxiety medications may be used to treat anxiety disorders, such as generalized anxiety disorder or panic disorder. They may also help reduce agitation and insomnia. Long-term anti-anxiety drugs typically include antidepressants that also work for anxiety. Anti-anxiety medications may include benzodiazepines, beta blockers, tricyclic antidepressants, monoamine oxidase inhibitors, selective serotonin reuptake inhibitors, serotonin and norepinephrine reuptake inhibitors, anticonvulsants, and mild tranquilizers. Exemplary anti-anxiety medication may include Armodafinil (Nuvigil®), Clonazepam (Klonopin®), Clorazepate (Tranxene®), Chlordiazepoxide (Librium®), Desipramine (Norpramin®), Diazepam (Valium®), Lorazepam (Ativan®), Alprazolam (Xanax®), Buspirone (Buspar®), Modafinil (Provigil®), Oxazepam (Serax®), Flurazepam (Dalmane®), Hydroxyzine (Atarax®, Vistaril®), Temazepam (Restoril®), Triazolam (Halcion®), and Zolpidem (Ambien®).

Antipsychotic medications typically may be used to treat psychotic disorders. Antipsychotic medications also may be used to treat bipolar disorders or used with antidepressants to treat depression. Exemplary first generation and second generation antipsychotic medications include, but are not limited to, Aripiprazole (Abilify®), Asenapine (Saphris®), Brexpiprazole (Rexulti®), Fluphenazine (Prolixin®), Quetiapine (Seroquel®), Olanzapine (Zyprexa®), Risperidone (Risperdal®), Clozapine (Clozaril®), Ziprasidone (Geodon®), Paliperidone (Invega®), Iloperidone (Fanapt®), Asenapine (Saphris®), Lurasidone (Latuda®), Chlorpromazine (Thorazine®), Haloperidol (Haldol®), Pimozide (Orap®), Thioridazine (Mellaril®), and Vortiozetine (Brintellix®).

Mood stabilizing medications, for example, may be used to treat bipolar disorders, which involves alternating episodes of mania and depression. Mood stabilizers also may be used with antidepressants to treat depression. Exemplary mood stabilizing medications include Lamotrigine (Lamictal®), Divalproex sodium (Depakote®), Carbamazepine extended release (Equetro®), Lithium (Eskalith®), and Lithium carbonate (Lithobid®).

Stimulants may be used, for example, to treat Attention-Deficit Hyperactivity Disorder (ADHD) and the like. Exemplary stimulant medications may include, but are not limited to, Amphetamine salt (Adderall®, Adderall XR®), Dexmethylphenidate (Focalin®), Clonidine (Kapvay®), Guanfacine (Intuniv®), Methylphenidate (Aptensio®, Concerta®, Daytrana®, Mixed salts of a single-entity amphetamine product (Mydayis®), Metadate®, Methylin®, Quillivant XR®, Quillichew ER®, Ritalin®), Dextroamphetamine (Dexedrine, ProCentra®), and Lisdexamfetamine (Vyvanse®).

More specific embodiments of the invention will now be described. While the following example involves differentiating BD from MDD and predicating an appropriate medication-class response, such an example is merely exemplary and should not be construed to limit the invention in any way.

Use of certain embodiments of the invention to differentiate BD from MDD may begin with examination of various subjects—aged 16-27—and subsequent categorization according to mental health into four categories: 32 with BD Type I (BD); 34 with MDD; and 33 HCs. BD and MDD patients were recruited from the First Episode Mood and Anxiety Program (FEMAP), and the psychiatric services at London Health Sciences Centre, London, Ontario, Canada. HCs were recruited from the general community. Diagnoses may be made using the *Structured Clinical Interview for DSM disorders-IV, (SCID-IV)*, First et al., Washington, DC: American Psychiatric Press, 1996, or the *Diagnostic Interview for Genetic Studies (DIGS)*, (Nurnberger et al. *Arch Gen Psychiatry* 1994; 51:849-859) plus psychiatric assessment (patient groups only). Agreement between clinical diagnosis and SCID/DIGS diagnosis of MDD or BD-type I was required for these patient groups. No participant was included in the MDD group if they had a family history of BD by the Family Interview for Genetic Studies (FIGS), (Maxwell et al., NIMH Molecular Genetics Initiative, 1992) or if the patient met screening criteria for BD as per the Composite International Diagnostic Interview based Borderline Personality Disorder screening scale. Participants in the HC group were excluded if they had a family history of mood disorders.

Inability to meet the inclusion criteria above led to creation of an "unknown" (UNK) group of 12 participants. Reasons for classification as UNK were prospective: disagreement between DIGS (no UNK participant underwent the SCID-IV) and psychiatrist diagnosis, first degree relative with mental disorder (recruited as HC), or uncertain diagnosis on psychiatrist evaluation, or retrospective reasons for classification as UNK include changes in diagnosis over the course of treatment or a response to a medication-class inconsistent with DSM diagnosis.

Various methods may be used to determine medication-class response. For example, chart review may be used to determine the medication-class used to help each patient in the UNK group attain sustained euthymia, as evaluated by the treating clinician, lasting at least six months. Medication-class also may be simplified to, for example, either an antidepressants or mood stabilizers (lithium, lamotrigine, carbamazepine, divalproex sodium).

Preferably, medications remain unchanged for three weeks prior to undergoing fMRI scanning. The mood of each subject was euthymic at the time of the scan as evaluated with the Montgomery-Asberg Depression Rating Scale and Young Mania Rating Scale. Some individuals in the UNK group had relapses following the scan and underwent a medication change to result in sustained (over 3 months) euthymia.

MRI images then may be collected from each group. Suitable MRI scanners include, but are not limited to, a 3.0 T Siemens Verio MRI scanner at the Lawson Health Research Institute using a 32-channel phased-array head coil. A T1-weighted, 3D magnetization-prepared rapid gradient echo sequence was used for anatomical images. Acquisition parameters were: repetition time (TR)=3000 ms, echo time (TE)=2.98 ms, flip angle=9°, field of view (FOV)=256 mm×256 mm, matrix size=256×256, 176 sagittal slices, voxel size=1 mm×1 mm×1 mm. Functional scans were gradient-echo, echo-planar scans with TR=2000 ms, TE=30 ms, flip angle=90°, FOV=240 mm×240 mm, matrix size=80×80, 40 axial slices and thickness=3 mm, with no parallel acceleration. A "voxel" as used herein is a three dimensional pixel residing at a particular (Y, Y, Z) coordinate and having one or more descriptive values, such as intensity. Raw fMRI image data of the human brain may now be characterized by a large number of voxels. Scans covered whole brain with an isotropic spatial resolution of 3 mm for a total time of approximately 8 min (164 brain volumes). No participant reported falling asleep during the scan when asked immediately after scanning. Four individuals were scanned twice: three BD patients scanned one, two or three years after their original scan; and one MDD patient scanned two years later. The repeat scans were accepted into the analysis to increase data available to train the classifier, result in 35 BD scans, 35 MDD scans and 33 HC scans. Embodiments of the invention were tested both with and without these replication scans and results were no different by t-test (p=0.68), so they were included.

The fMRI images may be preprocessed using statistical parametric mapping software known in the art such as, for example, SPM12, (http://www.fil.ion.ucl.ac.uk/spm/). To allow for magnetization equilibrium, the first ten images were discarded. The remaining 154 images were first corrected for the acquisition time delay among different slices and realigned to the first volume for head-motion correction. The fMRI images were spatially normalized to Montreal Neurological Institute (MNI) space by diffeomorphic anatomical registration using exponentiated Lie algebra (DARTEL) and spatially smoothed with a 6 mm FWHM Gaussian kernel. (Ashburner et al., *A fast diffeomorphic image registration algorithm*. Neuroimage. 2007 Oct. 15; 38(1):95-113. Epub 2007 Jul. 18).

Figure 3A:
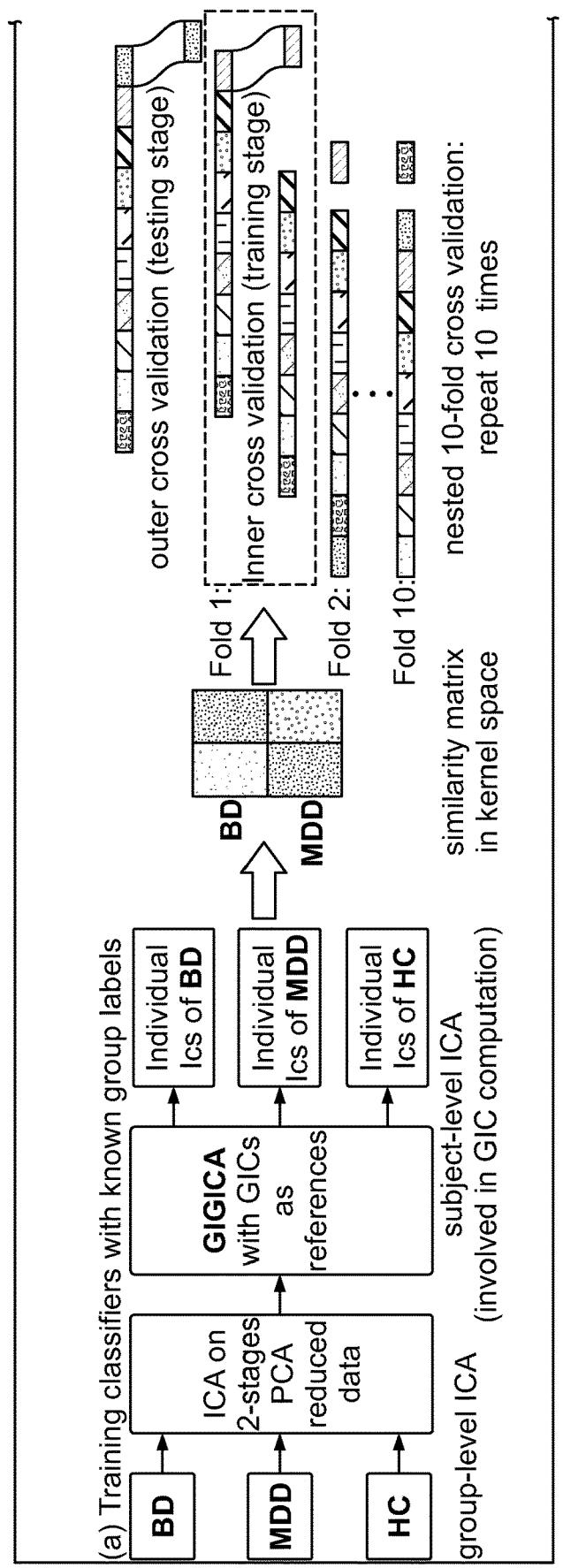
FIG. 3A illustrates a flowchart of one preferred embodiment of the invention that may be used to generate training classifiers for predicting a mental disorder of subjects with known group labels. Group ICA may be computed on temporally concatenated fMRI data of BD patients, MDD patients, healthy controls (HCs) resulting in individual subject maps computed by GIG-ICA. The unknown (UNK) subjects were not involved in the computation of the group-level ICA. For each cross-validation loop, similarity matrices for BD, MDD may be computed and classified via a kernel support vector machine (SVM) from the hold-out data using 10-fold cross validation.
Figure 3A:
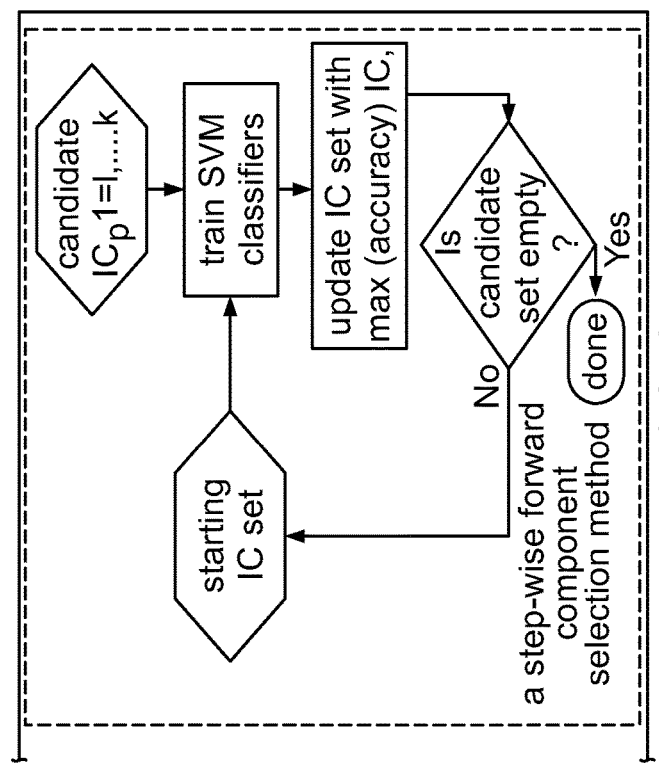

As shown in FIG. 3A, embodiments of a classification method according to the invention may include at least four parts: estimating maximally spatially independent components (ICs) from fMRI data (left), constructing a similarity matrix between subjects (Middle), partitioning the matrix in kernel space, and nested cross-validation of the support vector machine (SVM) classifiers and IC combinations (right). The dotted box on the right performs selection of the most relevant ICs within the cross-validation framework.

Advantageously, such an approach uses multiple fMRI ICs to build linear subspaces that may be calculated by adopting a principal angle based Riemannian distance for each individual subject or patient that may facilitate a comprehensive characterization of fMRI data for individuals. Then, in conjunction with an SVM classifier, a forward component selection technique may be selected from optimal ICs for constructing the most group-discriminative combinations and determined the final prediction of mental disorder and medication-class response of UNK by majority voting. The (cross-validated) training of the known BD/MDD/HC and the prediction of the UNK individuals were totally separated from each another. The prediction of the UNK individuals used the final group IC-based classifier extracted from the trained BD/MDD/HC stage.

FIG. 3A shows the schematic flowchart of group information guided ICA (GIG-ICA) to identify subject-specific component maps. As an extension of regular group ICA which incorporates an initial ICA to identify group spatial maps, GIG-ICA used the group component map as the reference to back-reconstruct individual subject components using spatially constrained ICA. The advantage of GIG-ICA is that the estimated individual IC maps are more accurate and robust and may be able to estimate corresponding-matched components from new data sets—the unknown subjects in this case—for classification purposes. GIG-ICA was performed for HC, BD and MDD, respectively, to build group-specific individual ICs, while the UNK subjects were not included, to avoid potential bias. 20 ICs were then choses to reduce computational complexity, similar to typical ICA based fMRI studies.

A subspace spanned by a combination of discriminative ICs was used to analyse the subspace similarity between individuals in order to determine optimal IC combinations, and thereby the highest classification accuracy. This subspace representation of ICs conveyed richer information in a concise manner, compared with treating ICs as voxel-wise spatial maps. A measure of Riemannian similarity/distance may be computed based on principal angles between spatial component maps of different individuals, representing subspace similarities between individuals spanning a subset of ICs. As shown in FIG. 3A, the subspace similarity may be represented by a symmetric matrix, which may be computed from ICs of BD and MDD individuals using the described methods.

According to embodiments of the invention, the maximally spatially independent components from fMRI data may be estimated such that fMRI data from each subject may be represented as a (t×v) matrix, where t is the number of time points and v is the number of in-brain voxels. The 4D resting-state fMRI data is represented as a matrix denoted by the (t×v) matrix X. The ICA model is then $$X = A \cdot S \qquad (1)$$

where A is the (t×c) mixing matrix and S is the (c×v) source signal matrix, and each row of the matrices is an IC corresponding to a specific functional brain network. The component number c is a free parameter which may be estimated using information theoretic approaches or determined using prior knowledge about functional brain networks.

An extension of this is group ICA which incorporates an initial ICA to identify group spatial maps, followed by a back-reconstruction step to estimate individual subject components. For the latter step, a spatially constrained ICA was used that enabled the use of component maps estimated from either a separate data set or from the data at hand, followed by individual subject ICA using these maps as a spatial constraint. The advantage of this approach is that the component ordering is comparable across subjects in addition to enabling us to estimate matched components from new data sets for classification purposes. FIG. 3A shows the schematic flowchart of GIC-ICA used in the BD and MDD classification scheme.

The initial group component maps are estimated from healthy controls (HC). The UNK fMRI data were not included in the group independent analysis to avoid potential bias. The HC component maps may then be used as spatial constraints for GIG-ICA estimated from a set of BD, MDD, and HC data sets which are used as references for the subsequent classification of the UNK individuals. This results in a set of component maps from each subject.

The subspace similarity—that is, the similarity matrix S—between different subjects may be calculated for different linear combinations of ICs using a subspace distance metric. For this purpose, a distance-based projection metric (Hamm et al., *Grassmann discriminant analysis: a unifying view on subspace-based learning*, International Conference 2008. pp. 376-383) was used and defined as $$d_p = \left(\sum_{i=1}^{k} \sin^2 \theta_i\right)^{\frac{1}{2}} = \left(k - \sum_{i=1}^{k} \cos^2 \theta_i\right)^{\frac{1}{2}}, \quad (2)$$

where p is short for projection, k is the number of subspace dimensions and $\theta_i$ is the principle angle of two k-dimensional subspaces, and i is an index of summation. $\theta_i$ is the principle angle of two k-dimensional subspaces. Given two subspaces $A=\{a_1, a_2, \ldots, a_k\}$ and $B=\{b_1, b_2, \ldots, b_k\}$, where $\{a_1, a_2, \ldots, a_k\}$ and $\{b_1, b_2, \ldots, b_k\}$ are orthonormal basis vectors (i.e., the component spatial maps) for subspaces A and B, the principle angles $$0 \leq \theta_1 \leq \theta_2 \ldots \leq \theta_k \leq \frac{\pi}{2}$$

between two subspaces A and B are defined as $$\cos \theta_i = \max_{a_i \in A} \max_{b_i \in B} a_i' b_i = \max_{b_i \in B} \max_{a_i \in A} b_i' a_i, \quad (3)$$

$$\text{subject to } a_i' a_i = b_i' b_i = 1, \, a_i' a_j = b_i' b_j = 0, \, (i \neq j).$$

Principle angles may be computed from a singular value decomposition (SVD) of the dot multiplication of two subspaces. Cosines of principle angles may numerically correspond to ordered singular values of A'B, and thus $\Sigma_{i=1}^{k} \cos^2 \theta_i = \Sigma_{i=1}^{k} s_i$, where s=svd(A'B).

The subspace similarity between different subjects then may be defined as:

$$S_p = \left(\frac{1}{k}\sum_{i=1}^{k} \cos^2 \theta_i\right)^{\frac{1}{2}}, \quad (4)$$

where p is short for projection and k is the number of subspace dimensions. The number of BD, MDD patients and UNK individuals are l, m and n respectively, and a (l+m+n)-dimensional symmetric matrix may be constructed based on the similarity metric between different subjects according to equation 3 above.

The partition of the similarity matrix in kernel space—$S_p$— may be mapped into a high dimensional feature space via a sigmoid SVM kernel function, as defined, for example, in Fan et al. *Discriminant analysis of functional connectivity patterns on Grassmann manifold*. NeuroImage 2011; 56(4): 2058-67 (2011), resulting in:

$$K(A,B) \tan h(\gamma S(A,B)), \quad (5)$$

where S(A, B) is the similarity in equation 3 and γ is the kernel parameter. This kernel function is used to build the SVM classifier. The SVM classifier was implemented by a library for support vector machines (LIBSVM, http://www.csie.ntu.edu.tw/~cjlin/libsvm/), and GIG-ICA was computed using the group ICA of fMRI toolbox (GIFT, http://mialab.mrn.org/software/gift). The kernel parameter was set to 1, and the trade-off parameter of all SVM classifiers was set to 10. The total number of independent components was set to 20 to reduce computational complexity.

Nested 10-fold cross validation with the disclosed methods was performed patients with a known BD and MDD diagnosis. In every training stage of the 10-fold cross validation, 9/10 of training data run another round of cross validation to choose the best combination of ICs which is a nested 10-fold cross validation. The individual scans building SVM similarity matrices in three stages are different as are the models trained in each of the three stages (the training and testing stage on BD, MDD patients and the diagnosing stage on UNK individuals). Thus, there are 10 optimal combinations of ICs and 100 SVM models for all 10 training sets in the training stage. This results in 90 classification results for each UNK individual and the final prediction of mental disorder and medication-class response is based on majority voting of all 90 results.

Additionally, a step-wise forward selection method such that, in each training step, a component in the candidate set was added to the optimizing component set and used to build a new component set. Kernel SVM classification may then be performed on test sets with known labels and selected the component with the highest accuracy to add into the optimization set. This process continued until the candidate set was empty (FIG. 3A). The classification performance may be estimated by averaging the classifiers' performance for all testing individuals. Comparing the classification performance of IC combinations with different IC numbers used in training identified the optimal group-discriminative IC combinations. Finally, ensemble classifier was constructed having a base classifier built with the 100 optimal IC combinations (10×10) from the training sets.

Figure 3B:
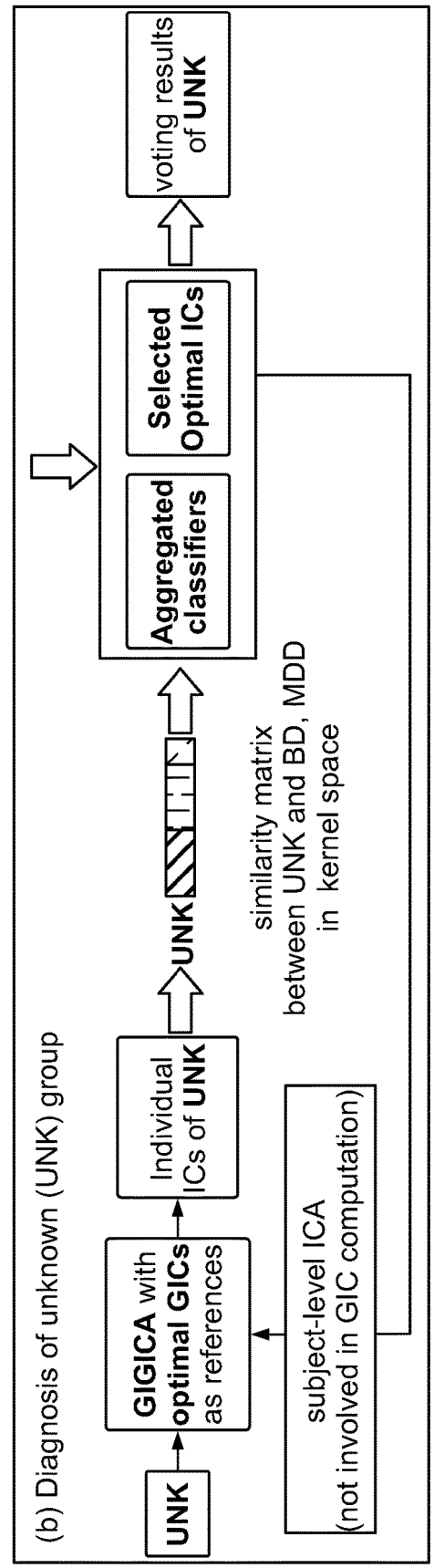
FIG. 3B illustrates a flowchart of one preferred embodiment of the invention showing the predicted diagnosis and medication-class response of subjects with unknown labels. A similarity matrix between the UNK and the BD and MDD individuals may be computed following group ICA and individual subject map calculation. Diagnosis of the UNK group may be based on a majority voting mechanism using an ensemble classifier.

Imaging analysts were blind to the medication-class of response in the UNK patients. As shown in FIG. 3B, the aggregated classifiers may be used to vote for the labels of each UNK patient for individual subject classification. Group membership for each new subject may be predicted by calculating their spatial components via GIG-ICA and entering each independently into the subspace representation. The UNK information was not use in either the training or testing stages, ensuring an unbiased prediction in the steps of FIG. 3B. Thus, each patient classification represented an individual test of the classification method at the single subject level. Classification vote was for either BD or MDD, as per the training set in the method, and this was compared with medication-class of response. A summary of known BD, MDD and HC participants' demographic information is illustrated in FIG. 5.

Figure 4A:
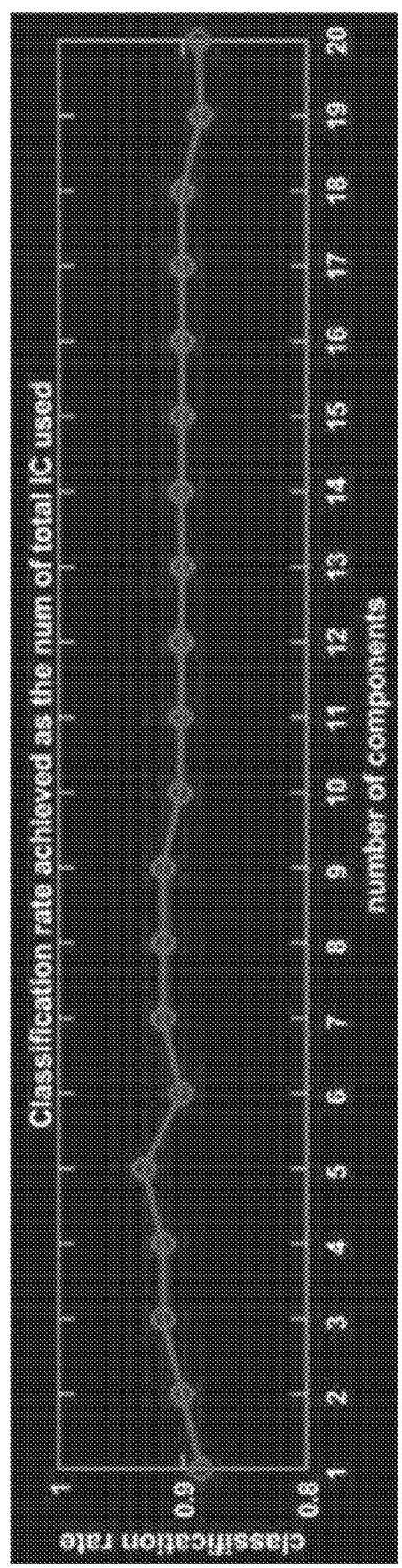
FIG. 4A illustrates classification rates achieved as a function of total number of Independent Components.

As shown in FIG. 4A, classification accuracies between known BD and MDD were all above 88% with different number of ICs used. The best classification rate, of 93.1% (sensitivity 86.5%, specificity 98.6%), was obtained using five ICs. Using these 5 ICs classification, accuracy between BD versus HC was 91.4% and between MDD versus HC was 94.2%. This was an improvement over previous approaches both in accuracy and time complexity, taking only 39.8 hours for one 10-fold cross validation versus 143.1 hours on a CentOS Linux computer cluster with 19 servers and 188 Intel Xeon CPUs.

Figure 4B:
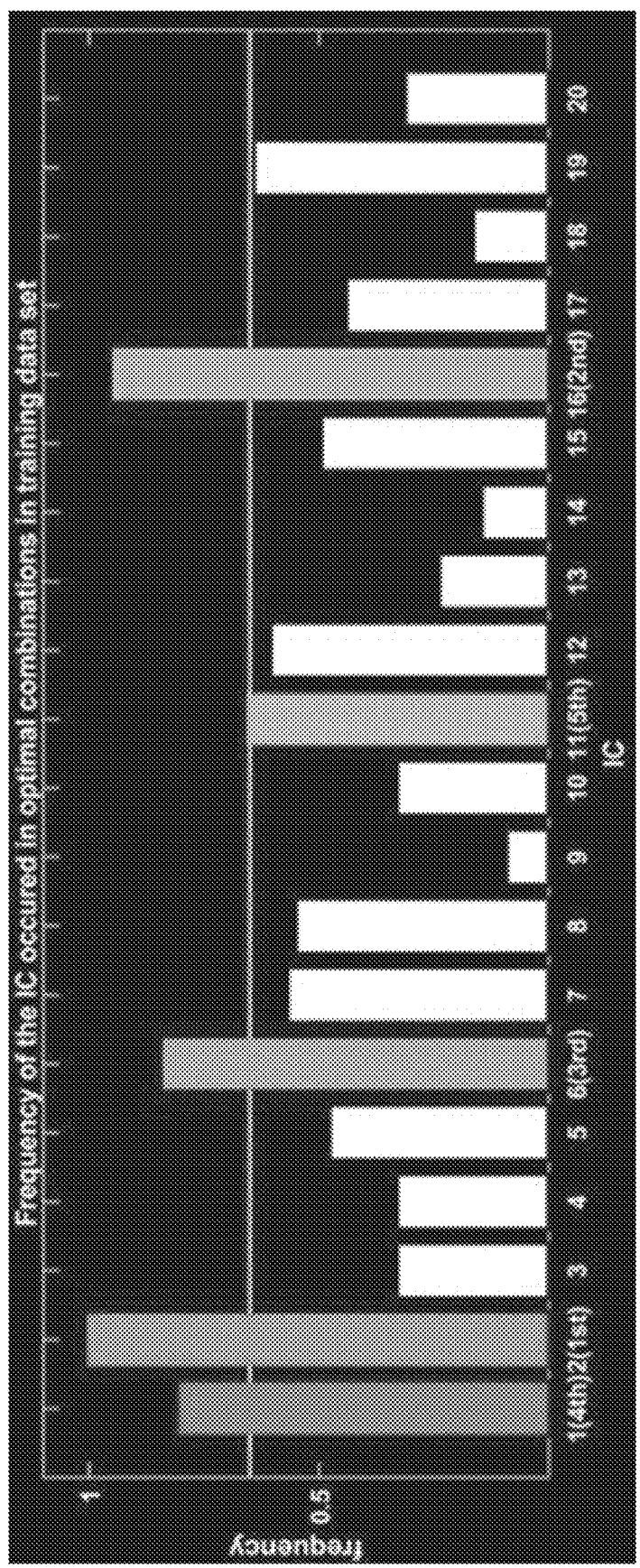
FIG. 4B illustrates the frequency of the Independent Components in 100 optimal combination.
Figure 4C:
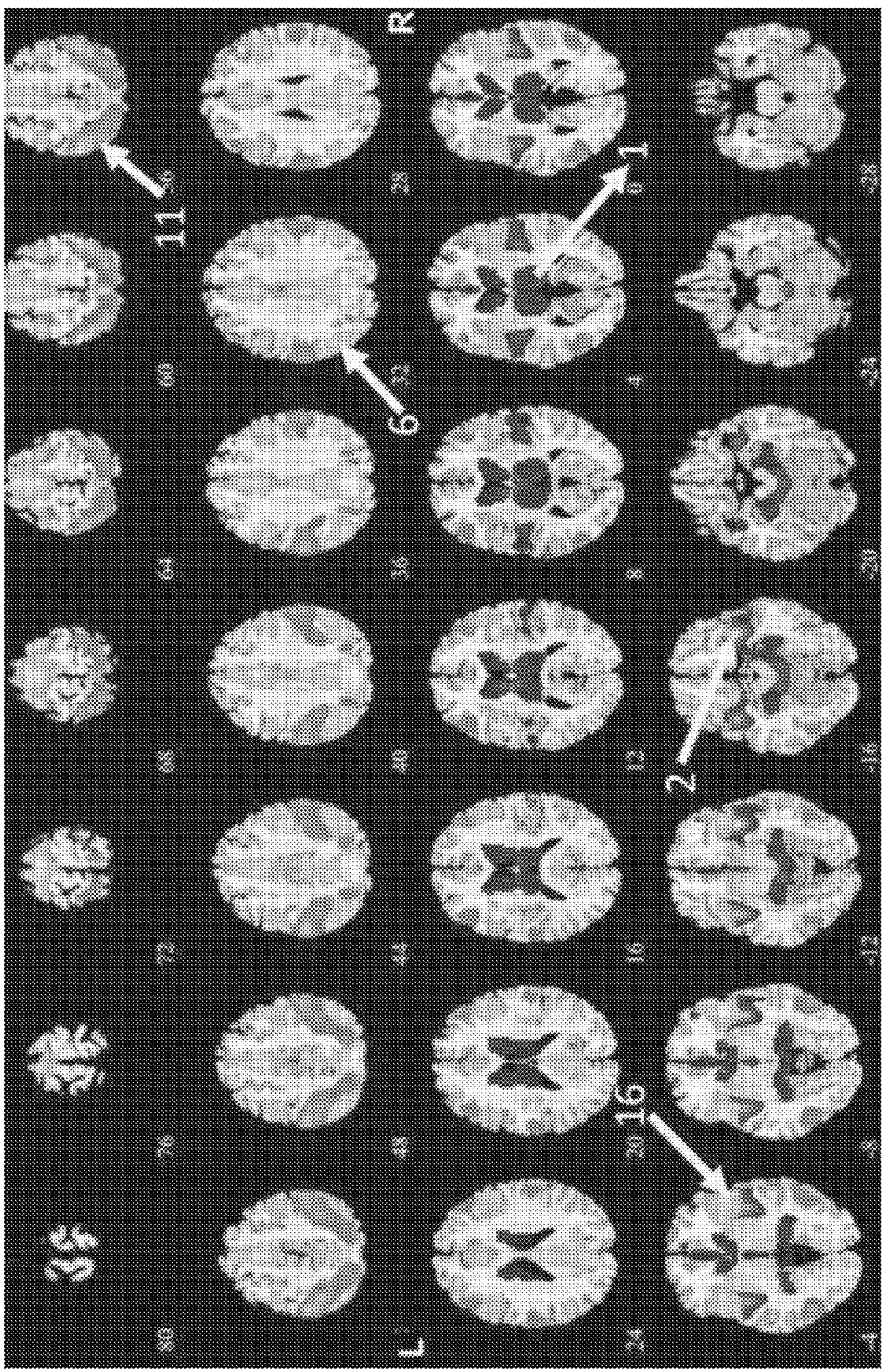
FIG. 4C illustrates a spatial overlay of Independent Components from FIG. 4B on a map of a brain.

In total, 100 combinations of ICs were extracted from ten times 10-fold cross validations. The frequency of all 20 components in best combination is shown in FIG. 4B. Five ICs were selected as the most discriminative functional networks for distinguishing BD from MDD (components 2, 16, 6, 1, 11; FIG. 4C). The five ICs cover several brain networks including the salience network (SN), dorsal attention network (DAN), frontoparietal central executive network (CEN), and the default mode network (DMN). They also included caudate, insula and thalamus.

The mean time between scan during euthymia and final chart review with sustained recovery was 608 days (standard deviation=509 days; range=153-1631). Voting ratios for BD versus MDD for each of the 12 UNK subjects, as well as the final classification prediction based on these ratios, clinical diagnoses, and medication-classes both during the scan and at sustained euthymia, and other variables are listed in FIG. 6.

The use of embodiments of the invention resulted in several noteworthy results. For example, subject 1308 was treated as MDD by a psychiatrist in a clinic, but euthymia was not sustained using any antidepressants. Eventually, the subject was stabilized on a single antipsychotic in another treatment setting. (The patient was never tried on a mood stabilizer.)

Subject 1322 had over five trials of antidepressants from multiple classes, alone and in combination, in combinations with antipsychotics, mood stabilizers, and light therapy as adjuncts; trial of electroconvulsive therapy (patient truncated after 8 sessions). The subject recovered only after all antidepressants were stopped to prepare for a monoamine oxidase inhibitor (MAOI); patient remained on a mood stabilizer (carbamazepine) and an antipsychotic (quetiapine). Quickly recovered completely so the MAOI was never tried; returned to work and school. The subject spontaneously stopped medication many months later, when euthymic, and was scanned. Shortly thereafter, the patient returned to clinic with a relapse and again recovered completely with carbamazepine and quetiapine, for a second full remission. Total time in clinic was over 4.5 years. The method voted BD, consistent with medication response. The subject showed no clinical symptoms of BD by the time of discharge.

Subject 1325—a "healthy control" with first-degree relative diagnosed with MDD after a suicide attempt—displayed a depressive episode in a 3 years after scan follow-up.

Subject 1349 was eventually diagnosed with schizoaffective disorder based on persistent paranoid ideation mentioned by mother after months of treatment at clinic. The one clear miss by the classification method.

Subject 1368, like subject 1322, revealed no clinical evidence of BD. The patient demonstrated severe depression and agitated, angry outbursts. Several antidepressants trialed but failed. Lithium was tried as a last effort before deciding that the patient had challenges beyond a mood disorder, including possible Asperger's syndrome. Lithium led to full recovery and independence with gainful employment. The prediction vote was again consistent with medication response.

Considering medication response as the "gold standard", the methods described herein were accurate for individual classification of 11 of 12 patients. Embodiments of the method correctly categorized five patients as having brain function "more like BD" patients who were mood stabilizers (plus one antipsychotic) responders; it correctly categorized as having brain function "more like MDD" two patients who were antidepressant responders; and it conservatively categorized four individuals who had sustained euthymia on no medication as having brain function more like MDD. It miss-categorized the one patient with schizoaffective disorder as more like MDD who actually required both a mood stabilizer and an antipsychotic for response and had not responded to an antidepressant.

Additionally, the methods of classification as described herein demonstrated 93% accuracy between the known participant BD and MDD groups used to train it. In the group of 12 complex patients, representative of individuals for whom a medication response prediction method is most needed, it correctly provided individual classification of the vast majority (92%), judging those with of sustained medication-class response to mood stabilizer and/or antipsychotic medications as more like BD and those without such a response as more like MDD. These findings also extend the understanding of the biological basis of medication-class responsiveness in mood disorders. Advantageously, such knowledge may improve both diagnostic strategies administered in the clinic and treatment for patients with complex presentations of mood disorders who may otherwise go unsuccessfully treated for years.

Two of the most clinically interesting cases presented here are 1322 and 1368. There was no clear symptomatology of BD in either individual before, during or after treatment. Both patients had non-response to antidepressants. Both would likely have been considered "treatment refractory" over time. In the case of 1322, it was only the removal of all antidepressants, with the retention of the mood stabilizers and antipsychotic, which led to full remission. He was scanned medication free. For 1368, depression was fully resolved with one medication, a mood stabilizer (though he was scanned on that medication). It is unclear how many individuals categorized as treatment refractory in routine clinical care might exhibit the same brain pathophysiology and therefore the same mental disorder classification and medication-class responsiveness as these patients.

Further, the psychiatrist was unclear of the specific mood diagnosis at the time of entry of six cases (1364, 1368, 1378, 1392, 1395, 1407). In four of those cases, the methods of the invention matched the medication-class of sustained response, attesting to the accuracy of the method for predicting medication responsiveness. In two of these cases, the methods of the invention indicated the brain function more like MDD, which was matched to sustained recovery with no medication. Since the method was binary for MDD or BD, this was the correct choice. MDD is more heterogeneous and more easily treated to remission without medication.

Individuals having no medication for a mood disorder at the time of sustained response (1325, 1372, 1378, 1395) were used as healthy controls. For example, participant 1325 was a "healthy control" with a first degree relative with MDD. This case had the lowest rating for BD-like brain function by the embodiments of the invention, and at post-study follow-up had had a depressive episode. Participant 1372 presented with complex symptoms and was diagnosed with generalized anxiety disorder and attention deficit hyperactivity disorder, but no primary mood disorder by the treating psychiatrist. Participants 1378 and 1395 were very similar to each other in having an unclear presentation per the psychiatrist, a DIGS diagnosis of MDD and an method vote for brain function more like MDD. Neither required medication for sustained response; both had had a mood stabilizer trial that was discontinued because in neither case was it particularly helpful. These four individual cases demonstrate the specificity of the embodiments of the invention for BD-like brain function and an associated medication responsiveness while at the same time showing the methods of the invention may correctly identify individuals as "not like BD".

Using certain embodiments of the invention, five ICs were determined to be the most salient for classification. The first (IC2) included temporal pole, inferior frontal gyrus and insula (FIG. 4A-C and FIG. 7), with one of the two critical nodes of the SN (insula). The other SN node (anterior cingulate cortex) appeared in IC16, the next most distinguishing component, which also included frontal portions of the CEN. Several areas in IC16 have consistently been associated with BD in structural brain studies. The third most discriminatory component (IC6) involved largely posterior brain regions of the DMN. The fourth contributing IC (IC1) included caudate body, thalamus and parahippocampal gyrus. The thalamus is the major relay/association structure for all somatic signals and includes areas controlling arousal and alertness. The caudate is a dopaminergic region involved in goal-directed action, emotion, motivation and memory and learning. Finally, the fifth IC (IC11) in the method contained all nodes of the DAN.

This combination of ICs, providing a data-driven grouping of brain regions, represents an interesting amalgamation of 'classic' large-scale brain network nodes. Three of four ICs identified include nodes of functional networks split between different ICs. The DAN was preserved only in one IC. Abnormalities in how these nodes sorted across ICs may pertain to the basic pathophysiology of mood disorders and may be particularly helpful for medication response prediction. There also were major contributions from autonomic processing regions, that is, the bilateral thalamus and insula. These regions were identified in meta-analyses showing lack of specificity of some brain networks to the common mental disorders.

Advantageously, embodiments of the invention may permit the reduction of hypothesis-bias so that the data may "draw its own conclusions" from the scans. The high accuracy of this method for the known mood diagnoses and for the individual classification for medication responsiveness of the complex patients was achieved, at least in part, by not being restricted to established functional networks or theoretical biases.

In the group of complex patients presenting with unclear diagnoses, the methods described herein correctly provided correct individual classifications of medication response for 11 of 12 patients, with the remaining patient having a diagnosis that the method was not trained to classify. The true test of a classification method is in characterizing difficult patients at the individual level, where such a technique is most needed, and the question that any such method most urgently needs to answer is, "What medication-class is most likely to help my patient attain sustained recovery?" The methods presented here make headway towards these goals.

FIG. 8 illustrates an exemplary computer system 800 that may be used to implement the methods according to the invention. One or more computer systems 800 may carry out the methods presented herein as computer code.

Computer system 800 includes an input/output display interface 802 connected to communication infrastructure 804—such as a bus—which forwards data such as graphics, text, and information, from the communication infrastructure 804 or from a frame buffer (not shown) to other components of the computer system 800. The input/output display interface 802 may be, for example, a keyboard, touch screen, joystick, trackball, mouse, monitor, speaker, printer, any other computer peripheral device, or any combination thereof, capable of entering and/or viewing data.

Computer system 800 includes one or more processors 806, which may be a special purpose or a general-purpose digital signal processor that processes certain information. Computer system 800 also includes a main memory 808, for example random access memory ("RAM"), read-only memory ("ROM"), mass storage device, or any combination of tangible, non-transitory memory. Computer system 800 may also include a secondary memory 810 such as a hard disk unit 812, a removable storage unit 814, or any combination of tangible, non-transitory memory. Computer system 800 may also include a communication interface 816, for example, a modem, a network interface (such as an Ethernet card or Ethernet cable), a communication port, a PCMCIA slot and card, wired or wireless systems (such as Wi-Fi, Bluetooth, Infrared), local area networks, wide area networks, intranets, etc.

It is contemplated that the main memory 808, secondary memory 810, communication interface 816, or a combination thereof, function as a computer usable storage medium, otherwise referred to as a computer readable storage medium, to store and/or access computer software including computer instructions. For example, computer programs or other instructions may be loaded into the computer system 800 such as through a removable storage device, for example, a floppy disk, ZIP disks, magnetic tape, portable flash drive, optical disk such as a CD or DVD or Blu-ray, Micro-Electro-Mechanical Systems ("MEMS"), nanotechnological apparatus. Specifically, computer software including computer instructions may be transferred from the removable storage unit 814 or hard disc unit 812 to the secondary memory 910 or through the communication infrastructure 804 to the main memory 808 of the computer system 800.

Communication interface 816 allows software, instructions and data to be transferred between the computer system 800 and external devices or external networks. Software, instructions, and/or data transferred by the communication interface 816 are typically in the form of signals that may be electronic, electromagnetic, optical, or other signals capable of being sent and received by the communication interface 816. Signals may be sent and received using wire or cable, fiber optics, a phone line, a cellular phone link, a Radio Frequency ("RF") link, wireless link, or other communication channels.

Computer programs, when executed, enable the computer system 800, particularly the processor 806, to implement the methods of the invention according to computer software including instructions.

The computer system 800 described herein may perform any one of, or any combination of, the steps of any of the methods presented herein. It is also contemplated that the methods according to the invention may be performed automatically or may be invoked by some form of manual intervention.

The computer system 800 of FIG. 8 is provided only for purposes of illustration, such that the invention is not limited to this specific embodiment. It is appreciated that a person skilled in the relevant art knows how to program and implement the invention using any computer system.

The computer system 800 may be a handheld device and include any small-sized computer device including, for example, a personal digital assistant ("FDA"), smart handheld computing device, cellular telephone, or a laptop or netbook computer, hand held console or MP3 player, tablet, or similar hand held computer device, such as an iPad®, iPad Touch® or iPhone®.

While the disclosure is susceptible to various modifications and alternative forms, specific exemplary embodiments of the invention have been shown by way of example in the drawings and have been described in detail. It should be understood, however, that there is no intent to limit the disclosure to the particular embodiments disclosed, but on the contrary, the intention is to cover all modifications, equivalents, and alternatives falling within the scope of the disclosure as defined by the appended claims.

Each of the cited references is incorporated herein by reference in its entirety.

The invention claimed is:

1. A method for predicting medication-class response to a mental disorder comprising:

collecting functional Magnetic Resonance Imaging (fMRI) scans of healthy subjects, known patients with a known mental disorder diagnosis and a medication-class response to the mental disorder, and unknown patients having an undiagnosed mental disorder, each scan comprising a plurality of images of one or more slices of a brain;

creating one or more databases of training data, the training data comprising the fMRI scans of healthy subjects and the known patients with a known mental disorder diagnosis and a medication-class response to the mental disorder;

pre-processing of the plurality of images from the training data of the one or more databases and creating one or more prior maps of optimal functional connectivity networks of the brain from the training data comprising the steps of:

estimating maximally spatially independent components (ICs) from the fMRI scans using a spatially constrained independent component analysis (ICA), the estimating step further comprises the step of representing each of the plurality of images as a (t×v) matrix, wherein t is the number of time points and v is the number of in-brain voxels, and a 4D resting-state fMRI data is represented as a matrix denoted by the (t×v) matrix X, the ICA is represented by a model X=A·S wherein A is the (t×c) mixing matrix and S is the (c×v) source signal matrix, and each row of the model is an IC corresponding to a specific functional brain network;

constructing a similarity matrix between the healthy subjects and the know patients based on the spatially constrained ICA;

partitioning the similarity matrix in kernel space;

selecting a step-wise forward component;

generating a classifier using the one or more prior maps of optimal functional connectivity networks of the brain;

applying the classifier to the fMRI scans of the unknown patients to calculate an output; and predicting the mental disorder and the medication-class response for the unknown patients based upon the output.

2. The method of claim 1, wherein the pre-processing step of fMRI scans from training data further comprises:

correcting each of the plurality of images for an acquisition time delay amount for each of the one or more slices of the brain;

realigning each of the one or more images to a first volume;

normalizing each of the one or more images to Montreal Neurological Institute (MNI) space by diffeomorphic anatomical registration using exponentiated Lie algebra (DARTEL); and spatially smoothing each of the one or more images at the half maximum (FWHM) Gaussian kernel.

3. The method of claim 1, wherein the generating step further comprises constructing a final classifier consisting of one or more classifiers using optimal independent component combinations from the training data in spatial or temporal domains.

4. The method of claim 1, wherein the predicting step further comprises:

running spatially constrained independent component analysis using the prior maps; and using the classifier to predict the diagnosis and the medication-class response of the unknown patients.

5. The method of claim 1 further comprising calculating the similarity matrix S between healthy subjects and patients for different linear combinations of the ICs using a subspace distance metric defined by:

$$d_p = \left(\sum_{i=1}^{k} \sin^2 \theta_i\right)^{\frac{1}{2}} = \left(k - \sum_{i=1}^{k} \cos^2 \theta_i\right)^{\frac{1}{2}},$$

where p is short for projection, k is the number of subspace dimensions and $\theta_i$ is the principle angle of two k-dimensional subspaces, and i is an index of summation.

6. The method of claim 5 wherein a subspace A={$a_1$, $a_2$, ..., $a_k$} and a subspace B={$b_1$, $b_2$, ... $b_k$} are orthonormal basis vectors for each of the subspace A and the subspace B, and principle angles $0 \leq \theta_1 \leq \theta_2 \ldots \leq \theta_k \leq \pi/2$ between the subspace A and the subspace B are defined as:

$$\cos \theta_i = \max_{a_i \in A} \max_{b_i \in B} a_i' b_i = \max_{b_i \in B} \max_{a_i \in A} b_i' a_i,$$

$$\text{subject to } a_i' a_i = b_i' b_i = 1, a_i' a_j = b_i' b_j = 0, (i \neq j).$$

7. The method of claim 6 wherein a cosine of the principle angles numerically corresponds to an ordered singular value of A'B defined by:

$$\Sigma_{i=1}^{k} \cos^2 \theta_i = \Sigma_{i=1}^{k} s_i, \text{ where } s = svd(A'B).$$

8. The method of claim 7 wherein a subspace similarity between the healthy subjects and the known patients is defined as:

$$S_p = \left(\frac{1}{k}\sum_{i=1}^{k} \cos^2\theta_i\right)^{\frac{1}{2}},$$

wherein p is short for projection and k is a number of subspace dimensions.

9. The method of claim 8, wherein the subspace similarity between the health subjects and the known patients is mapped into a high-dimensional feature space through the use of a sigmoid Support Vector Machine kernel function according to the following:

$K(A,B)=\tanh(\gamma S(A,B))$, wherein S(A, B) is the similarity of the subspace A and the subspace B and γ is a kernel parameter.

10. A method for predicting medication-class response to a mental disorder comprising:
  collecting functional Magnetic Resonance Imaging (fMRI) scans of healthy subjects, known patients with a known mental disorder diagnosis and a medication-class response to the mental disorder, and unknown patients having an undiagnosed mental disorder, each scan comprising a plurality of images of one or more slices of a brain;
  creating one or more databases of training data, the training data comprising the fMRI scans of healthy subjects and the known patients with a known mental disorder diagnosis and a medication-class response to the mental disorder;
  pre-processing of the plurality of images from the training data of the one or more databases and creating one or more prior maps of optimal functional connectivity networks of the brain from the training data comprising the steps of:
    estimating maximally spatially independent components (ICs) from the fMRI scans using a spatially constrained independent component analysis (ICA), wherein the estimating step further comprises the step of representing each of the plurality of images as a (t×v) matrix, wherein t is the number of time points and v is the number of in-brain voxels, and
    constructing a similarity matrix between the healthy subjects and the known patients based on the spatially constrained ICA;
    partitioning the similarity matrix in kernel space; and
    selecting a step-wise forward component;
  generating a classifier using the one or more prior maps of optimal functional connectivity networks of the brain;
  applying the classifier to the fMRI scans of the unknown patients to calculate an output; and
  predicting the mental disorder and the medication-class response for the unknown patients based upon the output.

11. The method of claim 10, wherein a 4D resting-state fMRI data is represented as a matrix denoted by the (t×v) matrix X, the ICA is represented by a model X=A·S wherein A is the (t×c) mixing matrix and S is the (c×v) source signal matrix, and each row of the model is an IC corresponding to a specific functional brain network.

12. The method of claim 10, wherein the pre-processing step of fMRI scans from training data further comprises:
  correcting each of the plurality of images for an acquisition time delay amount for each of the one or more slices of the brain;
  realigning each of the one or more images to a first volume;
  normalizing each of the one or more images to Montreal Neurological Institute (MNI) space by diffeomorphic anatomical registration using exponentiated Lie algebra (DARTEL); and
  spatially smoothing each of the one or more images at the half maximum (FWHM) Gaussian kernel.

13. The method of claim 10, wherein the generating step further comprises constructing a final classifier consisting of one or more classifiers using optimal independent component combinations from the training data in spatial or temporal domains.

14. The method of claim 10, wherein the predicting step further comprises:
  running spatially constrained independent component analysis using the prior maps; and
  using the classifier to predict the diagnosis and the medication-class response of the unknown patients.

15. The method of claim 10 further comprising calculating the similarity matrix S between healthy subjects and patients for different linear combinations of the ICs using a subspace distance metric defined by:

$$d_p = \left(\sum_{i=1}^{k} \sin^2\theta_i\right)^{\frac{1}{2}} = \left(k - \sum_{i=1}^{k} \cos^2\theta_i\right)^{\frac{1}{2}},$$

where p is short for projection, k is the number of subspace dimensions and $\theta_i$ is the principle angle of two k-dimensional subspaces, and i is an index of summation.

16. The method of claim 15 wherein a subspace A={$a_1, a_2, \ldots, a_k$} and a subspace B={$b_1, b_2, \ldots, b_k$} are orthonormal basis vectors for each of the subspace A and the subspace B, and principle angles $0 \leq \theta_1 \leq \theta_2 \ldots \leq \theta_k \leq \pi/2$ between the subspace A and the subspace B are defined as:

$$\cos\theta_i = \max_{a_i \in A} \max_{b_i \in B} a'_i b_i = \max_{b_i \in B} \max_{a_i \in A} b'_i a_i,$$

subject to $a'_i a_i = b'_i b_i = 1$, $a'_i a_j = b'_i b_j = 0$, $(i \neq j)$.

17. The method of claim 16 wherein a cosine of the principle angles numerically corresponds to an ordered singular value of A'B defined by:

$\Sigma_{i=1}^{k} \cos^2 \theta_i = \Sigma_{i=1}^{k} s_i$, where $s=svd(A'B)$.

18. The method of claim 17 wherein a subspace similarity between the healthy subjects and the known patients is defined as:

$$S_p = \left(\frac{1}{k}\sum_{i=1}^{k} \cos^2\theta_i\right)^{\frac{1}{2}},$$

wherein p is short for projection and k is a number of subspace dimensions.

19. The method of claim 18, wherein the subspace similarity between the health subjects and the known patients is mapped into a high-dimensional feature space through the use of a sigmoid Support Vector Machine kernel function according to the following:

$K(A,B)\tanh(\gamma S(A,B))$, wherein S(A, B) is the similarity of the subspace A and the subspace B and $\gamma$ is a kernel parameter.

* * * * *